US010309926B2

(12) United States Patent
Jansson et al.

(10) Patent No.: US 10,309,926 B2
(45) Date of Patent: Jun. 4, 2019

(54) ON CHIP CONTROL OF FLUIDS USING ELECTRODES (71) Applicant: GINOLIS OY, Oulunsalo (FI)

(72) Inventors: Fredrik Jansson, Stockholm (SE); Magnus Molin, Stockholm (SE)

(73) Assignee: GINOLIS OY, Oulunsalo (FI)

( * ) Notice: Subject to any disclaimer, the term of this patent is extended or adjusted under 35 U.S.C. 154(b) by 366 days.

(21) Appl. No.: 14/425,387

(22) PCT Filed: Sep. 3, 2013

(86) PCT No.: PCT/EP2013/068201
§ 371 (c)(1),
(2) Date: Mar. 3, 2015

(87) PCT Pub. No.: WO2014/033329
PCT Pub. Date: Mar. 6, 2014

(65) Prior Publication Data
US 2015/0204817 A1 Jul. 23, 2015

(30) Foreign Application Priority Data
Sep. 3, 2012 (EP) .................................. 12182729

(51) Int. Cl.
G01N 27/447 (2006.01)
B01L 3/00 (2006.01)
(Continued)

(52) U.S. Cl.
CPC .... *G01N 27/44791* (2013.01); *B01L 3/50273* (2013.01); *B01L 3/502784* (2013.01);
(Continued)

(58) Field of Classification Search
CPC ........... G01N 27/44791; B01L 3/50273; B01L 3/502784; F04B 19/006; F04B 43/043; B01F 13/0071–13/0076
See application file for complete search history.

(56) References Cited

U.S. PATENT DOCUMENTS

2006/0194331 A1* 8/2006 Pamula ............... B01F 13/0071
436/150
2008/0247920 A1* 10/2008 Pollack ............... B01F 11/0071
422/243
2008/0257438 A1* 10/2008 Wang ........................ F15C 5/00
137/833

FOREIGN PATENT DOCUMENTS

WO WO 00/44930 A1 8/2000
WO WO 2011/131795 A1 10/2011

OTHER PUBLICATIONS

International Search Report prepared by the European Patent Office dated Sep. 27, 2013, for International Application No. PCT/EP2013/068201.
(Continued)

*Primary Examiner* — Maris R Kessel
(74) *Attorney, Agent, or Firm* — Berg Hill Greenleaf Ruscitti, LLP.

(57) ABSTRACT

The present invention relates to a device for controlling movement of a fluid sample along a flow path and a corresponding method. The device comprises a working electrode (2) arranged to contact the fluid sample when the fluid sample moves along the flow path, and a reference electrode (3) arranged to contact the fluid sample when the fluid sample moves along the flow path. At least a portion of the reference electrode is arranged abreast of or downstream at least a portion of the working electrode. The present invention is advantageous in that it provides a device wherein a fluid sample may be transported and accurately
(Continued)

controlled, with respect to e.g. timing, volumes and flow rates, over greater distances compared to prior art.

15 Claims, 5 Drawing Sheets

(51) Int. Cl.
*F04B 19/00* (2006.01)
*F04B 43/04* (2006.01)

(52) U.S. Cl.
CPC .......... *F04B 19/006* (2013.01); *F04B 43/043* (2013.01); *B01L 2300/0887* (2013.01); *B01L 2400/0427* (2013.01)

(56) References Cited

OTHER PUBLICATIONS

Satoh Wataru et al: "Microfluidic transport based on direct electrowetting", Journal of Applied Physics, American Institute of Physics, New York, US, vol. 96, No. 1, Jul. 1, 2004, pp. 825-841.

* cited by examiner

ON CHIP CONTROL OF FLUIDS USING ELECTRODES

CROSS REFERENCE TO RELATED APPLICATIONS

This application is a national stage application under 35 U.S.C. 371 and claims the benefit of PCT Application No. PCT/EP2013/068201 having an international filing date of Sep. 3, 2013, which designated the United States, which PCT application claimed the benefit of European Patent Application filed Sep. 3, 2012, the disclosures of each of which are incorporated herein by reference.

TECHNICAL FIELD

The present invention relates to devices for controlling movement of fluid samples in microfluidic chips and to a method for controlling or manipulating a fluid flow through channels of such microfluidic chips. The microfluidic chips may be used in biotechnological, diagnostical and pharmaceutical applications.

BACKGROUND OF THE INVENTION

Microfluidics relates to a multidisciplinary field comprising physics, chemistry, engineering and biotechnology that studies the behavior and flow of fluids at nano and microliter scale inside open or closed microchannels. Microfluidics has enabled the development of so-called 'lab-on-a-chip' devices and systems that can process microliter and nanoliter volumes of sample fluid, and perform highly complex and sensitive analytical measurements. 'Lab-on-a-chip' indicates the scaling of single or multiple laboratory processes down to a chip-format, which is only millimeters to a few centimeters in size.

Microfluidic-based analysis chips and microfluidic-based diagnostic test chips (hereafter collectively referred to simply as 'chips') are used for a variety of biotechnological and diagnostic applications, such as nucleic acid detection, characterization, separation, sizing, and typing; cell manipulation and sorting; biomarker detection; microbial pathogen detection; and miniaturization of chemical synthesis.

Microfluidic-based chips offer many advantages over traditional macro-sized counterparts: Easy handling (less hands-on-time, and less sample and reagents are required) and rapid test results (shorter analysis times). The shorter analysis time and easy handling of microfluidic chips is attractive for diagnostic applications because it enables rapid bedside and doctor's office tests, offering the advantage of rapid test result that can be shared with the patient right away.

However, diagnostic applications require a strict control of the sample fluid flow within the chip in order to ensure the required accuracy and reproducibility of the analysis/test. Typically operations such as mixing; incubation; separation; and detection are performed within the chip, which demands firm control of the sample fluid flow in terms of timing, volumes and flow rates.

Various actuation mechanisms have been developed and are presently used, such as, for example, micropumps, microvalves, and rotary drives applying centrifugal forces. However, the mechanism mostly used in today's products is capillary driven flows, largely due to its simplicity.

In order to take control of the fluid flow in capillary driven microfluidic chips, passive control schemes relying on reproducible geometries and stabile surface properties has been developed. Time gates can be designed to slow down or stop the flow of a predetermined volume for a predetermined time and channels can be designed to have the right capillary force to drive the flow at a predetermined flow rate.

However, for diagnostic applications the variable composition and viscosity of biological samples puts up a major challenge to microfluidic assay development. Typical biological samples include e.g. saliva, urine, serum, plasma and whole blood, and they vary in composition and viscosity from individual to individual as well depending on when the sample was taken. These variations, along with variations in the surface properties of the microfluidic chips, causes variations in timing, volumes and flow rates and can thereby negatively affect the reproducibility of diagnostic microfluidic-based tests.

In order to achieve the firm control needed of the sample fluid flow, in terms of timing, volumes and flow rates in capillary driven microfluidic chips various wettability switches have been developed. A wettability switch allow for manipulation of a solid surface's ability to maintain contact with a liquid. The wettability is determined by a force balance between adhesive and cohesive forces when the solid switch surface is in contact with the liquid. Adhesive forces between the solid and the liquid cause a liquid drop to spread across the switch surface. Cohesive forces within the liquid cause the liquid drop to ball up and avoid contact with the switch surface. The force balance can be manipulated through various influences such as light, temperature, chemistry, electrochemistry or electric field. Within the area of microfluidics some kind of electronic influence is preferred due to its rapid actuation and low interference with the fluid.

One technology used for electronically altering the wettability of a surface is electrochemical electrowetting, where a voltage in the order of one volt is applied between a working electrode and a reference electrode, in electrical contact with each other through an electrolytical fluid, forming an electrochemical double layer at the surface of the work electrode that increases its wettability.

Another technology used for electronically altering the wettability of a surface is electrowetting on dielectric, where tens to hundreds of volts are applied between a working electrode and a reference electrode, electrically isolated from each other, forming a strong electric field that forces the droplet down towards the isolated work electrode surface.

A further technology used for electronically altering the wettability of a surface is electrowetting with ion-doped conducting polymers, where a few volts are applied between a working electrode doped with polar ions, having a hydrophobic and a hydrophilic end, and a reference electrode, making the polar ions shifting orientation and thus shifting the wettability of the work electrode surface.

For the flow control in continuous flow applications electrochemical electrowetting is preferred in its simplicity, amongst others due to a greater wettability change and a better long term stability compared to electrowetting using ion-doped conducting polymers and due to a low voltage need and cost effectiveness compared to electrowetting on dielectric.

Prior art within electrochemical electrowetting has described microfluidic chips having a reference electrode placed in the beginning of a flow path (microfluidic channel) followed by one or a few work electrodes downstream the flow path. The working electrodes are typically hydrophobic thus stopping the fluid in their natural state, but turn hydrophilic and let the fluid pass when a voltage is applied.

However, a major drawback with the electrochemical electrowetting microfluidics technology according to prior art is that the speed of the fluid flow front may rapidly decrease with the distance travelled along the flow path. About one centimeter into the channel, the electrically activated flow may more or less have ceased, thereby impeding activation of a switch.

One example of prior art is described by a research team from Tsukuba in Japan in the article Microfluidic transport based on direct electrowetting, J. Appl. Phys. 96, 835 (2004). The article describes a microfluidic chip of about 20×30 mm with a channel being about 18 mm long. An Au working electrode is covering the bottom of the channel and an Ag/AgCl reference electrode is placed upstream the working electrode.

In the article the research team conclude that when applying a voltage between the working electrode and the reference electrode the fluid front starts to move along the working electrode. However, they conclude that the speed of the fluid front decreases with the distance travelled in the channel and that the movement finally cease. In fact the research team concludes that the fluid front never reaches through the about 18 mm long channel.

The research team conclude that the decrease of the flow rate and final cease of the flow are due to the viscous resistance, which is said to increase linearly with the distance travelled. The research team further conclude that by working with microfluidic chips of about 10×10 mm this limitation might be acceptable.

However, a channel length limitation of about 1 cm is for practical reasons limiting the amount of sample fluid that is possible to handle (in terms of timing, volumes and flow rates), to nanoliter volumes rather than microliter volumes. When targeting applications within medical diagnostics this is a major drawback, since most point of care tests require a sample volume in the microliter range in order to produce accurate and reproducible results.

In reality, the channel length limitation is actually shorter than 1 cm when using the working electrode(s) for driving a flow within the channel. When targeting applications within medical diagnostics flow velocities of tens of millimeter per minute are typically required. Due to the rapid decrease of the flow velocity, the velocity of the fluid front is below what is required already a few millimeters into the channel.

The channel length limitation is for practical reasons also limiting the number of working electrodes that are possible to place along the flow path, given a certain minimal working electrode size possible to produce cost effectively (for instance the smallest working electrode possible to produce with a metal sputter mask instead of photolithography). When targeting medical diagnostics, multiple operations according to above need to be performed with firm and fine-tuned flow control. However, a limited number of fairly large working electrodes, relative to the length of the channel, is thus limiting the number of operations and the possibility of fine-tuned flow control.

Altogether, due to a channel length limitation of about 1 cm or even less, prior art has a limited ability to handle microliter volumes of sample fluid with the firm control of timing, volumes and flow rates required for many applications within medical diagnostics.

SUMMARY

An object of the present invention is to wholly or partly overcome the above drawbacks of the prior art and to provide an alternative to the above technique.

This and other objects are achieved by the present invention as defined by the independent claims. A selection of possible embodiments is defined by the dependent claims. However, as the skilled person will be aware of when studying the specification following hereinafter, there are a number of further and/or alternative embodiments of the present invention that are conceivable.

The inventors of the present invention have surprisingly found that the above mentioned limitations of the prior art not only depend on the viscous resistance, but is also depending on the design and placement of the electrodes, and that a new electrode setup may overcome the above mentioned limitations of the prior art.

Hence, according to a first aspect of the present invention, there is provided a device for controlling movement of a fluid sample along a flow path. The device comprises a working electrode arranged to contact the fluid sample when the fluid sample moves along the flow path, and a reference electrode arranged to contact the fluid sample when the fluid sample moves along the flow path. At least a portion of the reference electrode is arranged abreast of or downstream at least a portion of the working electrode.

According to a second aspect of the present invention, a method for transportation of a fluid sample along a flow path is provided. The method comprises the steps of providing a working electrode arranged to contact the fluid sample when the fluid sample moves along the flow path, and providing a reference electrode arranged to contact the fluid sample when the fluid sample moves along the flow path. At least a portion of the reference electrode is arranged abreast of or downstream at least a portion of the working electrode. The method may further comprise the steps of providing a fluid sample at one end of the flow path, and applying a voltage between the working electrode and the reference electrode. The applied voltage alters the wettability of the working electrode surface and thereby promotes advancement of the fluid front across the working electrode surface, along the flow path.

Thus, in contrast with prior art, where the reference electrode is placed upstream the working electrode(s), the present invention is based on the idea that by arranging at least a portion of a reference electrode abreast of or downstream an upstream end portion of a working electrode (which may be the first of several working electrodes along the flow path in the direction of the flow), the present invention may preserve the working electrode(s)'s capacity to change wettability along the flow path and may thereby overcome the channel length limitation of the prior art.

As an example, by arranging a reference electrode abreast of the working electrode (e.g. in the channel roof above the working electrode), the distance between the reference electrode and the working electrode may be limited as compared with the prior art, in which the distance between the working electrode and the upstream reference electrode tends to increase along the channel in the direction of the flow.

As another example, by arranging a reference electrode downstream a working electrode (e.g. downstream a first working electrode and upstream a second working electrode in the direction of the flow), the distance between each working electrode and a reference electrode may be limited as compared with the prior art, in which the distance between the working electrode and the upstream reference electrode tends to increase along the channel in the direction of the flow.

By reducing the distance between the working electrode(s) and the reference electrode(s), i.e. the distance over which a potential may be applied across the fluid, the potential drop across the fluid may be reduced. Thereby the working electrode(s)'s capacity to change wettability may be improved.

By preserving the ability to alter the wettability of the working electrode along the flow path the fluid sample may be transported and accurately controlled, with respect to e.g. timing, volumes and flow rates, over greater distances compared to prior art. The greater distance over which the fluid sample can be controlled enables, amongst others:

- Handling of sample fluid volumes in the microliter range (as needed for the accuracy in many point of care tests) due to the longer and wider channels possible. This is advantageous over the prior art, wherein sample volumes in the nanoliter range (which is insufficient for many point of care tests) are handled in short and narrow channels.
- Driving sample fluid flow with sufficient fluid front velocities over centimeter distances (as needed in many point of care tests) due to the preserved capacity to alter wettability along the flow path. This is advantageous over prior art, wherein the fluid front velocity drops below what is required for many point of care tests already after a few millimeters travelled.
- Controlling timing and volumes more reproducibly (as needed in many point of care tests) by being able to design more secure flow gates (i.e. stops) due to the preserved capacity to alter the wettability along the flow path and thereby the preserved ability to pass a secure flow gate. This is advantageous over prior art, wherein the ability to pass a flow gate quickly diminishes why the stopping ability of the flow gate therefore has to diminish equally in order to be passable, which in turn causes a less secure stop.
- Controlling flow in fine-tuned pulses in a pulsed flow setup where the fluid is let to propagate across several working electrodes along the flow path, one electrode at a time, in order to achieve a reproducible mean flow rate over centimeter distances (as needed in many point of care tests). This is advantageous over prior art, wherein each working electrode of the same size represents a larger part of a shorter channel and therefore causes a less fine-tuned pulsed flow and wherein the fluid front velocity drops below what is required already after a few millimeters travelled limiting the use of a pulsed flow setup.

Altogether, due to the preserved capacity to alter the wettability of the work electrode(s) along the flow path the present invention may overcome the above mentioned limitations of the prior art and may have the capability to handle microliter volumes of sample fluid with the firm control of timing, volumes and flow rates required for many applications within medical diagnostics.

By "electrode" should be understood any electrically connectable surface that is adapted to be in electrical contact with the sample fluid and an external power supply. The electrodes may for example be arranged at any surface facing the flow path.

A working electrode may be defined as an electrode that changes, or is adapted to change, wettability (or hydrophobicity/hydrophilicity) upon application of a voltage between the working electrode and a reference electrode. A reference electrode may be defined as an electrode acting as a counter (or auxiliary) electrode or a reference electrode of a working electrode upon application of a voltage between the working electrode and the reference electrode. It may also be a combined counter electrode and reference electrode. The electrical potential difference may be generated by an external voltage supply.

The working electrode and the reference electrode being arranged to contact the fluid sample when said fluid sample moves along the flow path means that the electrodes are so arranged along the flow path that they contact the fluid sample when the device of the invention is in use for controlling movement of a fluid.

It will also be appreciated that the reference electrode and the working electrode together may form a first pair of electrically related electrodes. However, the reference electrode and the working electrode might as well form parts of different electrode pairs, such as a second and a third pair, respectively.

Further, the device may comprise a plurality of working electrodes and/or a plurality of reference electrodes. The electrodes may also be arranged in pairs, or groups of three or more electrodes.

The flow path may be a longitudinal portion of the device along which portion the front surface of the fluid sample moves during use, thereby causing a subsequent flow or movement of the fluid sample. The flow path may comprise an inlet, adapted to receive a fluid and supply it to the flow path, and an outlet adapted to outlet a fluid (such as for example the fluid sample, or air). During use, the fluid may flow from the upstream end portion of the flow path towards the downstream end portion. This direction may also be referred to as the flow direction. The flow path may for example be a channel or a tube, fully or partly defined by portions of the electrodes or other suitable materials.

Controlling movement of the fluid comprises actuating and stopping the flow, which may be enabled by applying and not applying, respectively, a voltage between the working electrode and the reference electrode. The controlling of the movement may also include varying the velocity of the fluid flow, for example by increasing or decreasing the applied voltage.

By fluid should, in the context of the present invention, be understood any electrically conductive liquid, or electrolyte. This could for example include bodily fluids such as saliva, urine, serum, plasma, and full blood.

A portion of a reference electrode is arranged abreast of a portion of a working electrode. A portion of a reference electrode may also be arranged downstream of a portion of a working electrode. Downstream from a point along the flow path should, in this context, be understood as the part of the fluid path located after that point in the direction of flow, or movement, of a fluid when a device of the invention is in use for controlling movement of a fluid. Upstream from a point along the flow path should, in this context, be understood as the part of the fluid path located before that point in the direction of flow, or movement, of a fluid when a device of the present invention is in use for controlling movement of a fluid.

According to an embodiment of the present invention, the working electrode may be a plane electrode. This may also apply for the reference electrode. A plane electrode is preferably an electrode having a lateral extension that is larger than the thickness of the electrode, such as a lead deposited on a substrate. This embodiment is advantageous in that it may enable the electrode material to be applied to a surface of the flow path by sputtering, evaporation, screen printing, or other deposition techniques known in the art. The electrodes may advantageously be defined by patterning methods that are used for example in the electronics industry.

According to an embodiment of the present invention, the working electrode and the reference electrode may extend in separate planes, or surfaces. Each plane may for example be defined by a wall of a channel, correspondingly, wherein the working electrode may be arranged at a first wall, such as the bottom of the channel, and wherein the reference electrode may be arranged at a second wall, such as the opposing top wall (roof) of the channel. This embodiment is advantageous in that it may facilitate production of the electrodes, which may be manufactured in separate processes. Being able to use separate production methods for the working electrode and the reference electrode may be an advantage for example in the case when the working electrode and the reference electrode do not comprise the same material, or require different handling.

According to an embodiment of the present invention, the working electrode may be a longitudinal electrode in relation to the flow path. This may also apply for the reference electrode. A longitudinal electrode may, preferably, be an electrode having an extension in the flow direction (length) that is larger than the extension in a direction perpendicular to the fluid flow (width). The length of the electrode may for example be essentially equal to the length of the channel. It will also be appreciated that the device may comprise a plurality of working electrodes and reference electrodes. Longitudinal electrodes may be advantageous in that they may allow for the fluid sample to be actively transported over long distances along flow path.

According to an embodiment of the present invention, the device comprises at least two working electrodes and/or at least two reference electrodes which are consecutively arranged along the flow path. This may reduce the total electrode area and may, advantageously, allow for an individual application of voltage. A separate control of each or a group of electrodes may increase the control of the movement of the fluid during use of the device (e.g. a separate working electrode used as a flow gate/stop or several consecutively arranged working electrodes used for achieving a pulsed flow where the activation (application of a voltage) of each working electrode represents one flow pulse).

According to an embodiment of the present invention, the device may comprise at least two interdigitated electrodes. A work electrode may be interdigitated with a reference electrode or a second work electrode. Correspondingly, a reference electrode may be interdigitated with another reference electrode. It will be appreciated that the interdigitated electrodes may be longitudinal electrodes. This embodiment is advantageous in that it may enable an improved control of the fluid flow, as described in the above embodiment, yet still using a reduced number of electrical connections (for example one connecting pad per electrode).

According to an embodiment of the present invention, the device may comprise at least one reference electrode and at least two interdigitated working electrodes (interdigitated into each other). This embodiment is advantageous in that it may enable a fine-tuned pulsed flow with only one electrical contact pad for the first interdigitated working electrode, one electrical contact pad for the second interdigitated working electrode and one contact pad for the reference electrode. By applying a voltage between the first interdigitated working electrode and the reference electrode the sample fluid may pass the first "finger" of the first interdigitated working electrode, but may stop at the beginning of the first "finger" of the second interdigitated working electrode, since it may not yet be activated (i.e. no voltage applied on the second interdigitated working electrode). When the fluid has reached the first "finger" of the second interdigitated working electrode, the voltage between the first interdigitated working electrode and the reference electrode may be switched off. By then applying a voltage between the second interdigitated working electrode and the reference electrode the sample fluid may pass the first "finger" of the second interdigitated working electrode, but may stop at the beginning of the second "finger" of the first interdigitated working electrode, since it may not yet be activated. When the fluid has reached the second "finger" of the first interdigitated working electrode, the voltage between the second interdigitated working electrode and the reference electrode may be switched off. By activating one interdigitated working electrode at a time and drive the flow over that electrode's next "finger" and using the other interdigitated working electrode's next "finger" to stop the flow, a fine-tuned pulsed flow may be achieved over long distances with just three contact pads as described above. This is advantageous in that the flow can be controlled reproducibly and in that mean flow rate can be accurately controlled. The switching of the applied voltage may also include a time delay, such as a predetermined "idle time" during which the applied voltage is zero, or close to zero. This time delay may e.g. allow for a chemical reaction to occur, or a measurement to be performed, prior to further transportation.

According to an embodiment of the present invention, the flow path may be a channel. The channel may be defined by one or several walls, such as a bottom wall, two sidewalls, and a top wall. The walls may have hydrophilic portions, which may promote capillary flow of the sample fluid. The walls may also have hydrophobic portions, which may promote the flow of the sample fluid to decrease or cease. The channel may also have a circular, rectangular, or triangular cross section, or any other suitable shape that allows a flow of the fluid sample.

According to an embodiment of the present invention, the device may further comprise a fluid reservoir arranged to receive and accommodate the fluid sample, and from which the fluid front moves along the flow path. The reservoir may for example be a container or void that may communicate with the flow path such that a fluid sample can be supplied to the flow path. This embodiment is advantageous in that it may facilitate the application of the fluid sample, and that it may supply the flow path with an enough volume of the sample to enable a continuous fluid flow during use of the device or transportation of the fluid.

According to an embodiment of the present invention, the working electrode and/or the reference electrode may comprise at least a surface that is less prone to interfere with the fluid sample in a negative way, such as a biocompatible surface, and electrically conducting. It may also be possible to modify the wettability of the surface of the working electrode by altering an applied potential. Examples of such materials may include noble metals, carbon and allotropes of carbon, such as gold, platinum, iridium, osmium, silver, palladium, carbon, graphite, graphene, and fullerenes. Other examples may include electronically conducting polymers.

According to an embodiment of the present invention, the working electrode and/or the reference electrode may comprise a structured surface adapted to contact the fluid sample during use of the device. The structured surface may for example be a micro- and/or nanostructured surface (e.g. ridges, pillars, etc.). This embodiment is advantageous in that the structured surface may increase the hydrophobicity of the surface of the working electrode in its inactivated state (i.e. with no voltage applied). It may also increase the hydrophobicity of the reference electrode. Since the fluid front may tend to stop propagating as it encounters a hydrophobic surface, this embodiment may enable an improved ability of stopping, and thereby controlling, the fluid flow.

According to an embodiment of the present invention, the device may comprise at least one hydrophobic surface portion arranged to contact the fluid sample as it moves along the flow path, and wherein at least a portion of said hydrophobic surface portion is arranged abreast of at least a portion of the working electrode. Thereby the hydrophobic surface portion may cooperate with a working electrode such that the fluid sample, in case the working electrode e.g. is in a hydrophobic state, may be prevented from passing the hydrophobic surface portion and hence the control of the fluid flow may be improved. The hydrophobic surface portion may have a water contact angle (WCA) exceeding 80 degrees, such as exceeding 100 degrees WCA, and preferably exceeding 120 degrees WCA. The hydrophobic surface properties of the hydrophobic surface portion may depend on surface chemistry (e.g. fluorinated materials) or on pinning effects of micro/nano structures (e.g. ridges, pillars, etc.) or on a combination thereof. Pinning effect may as an example be understood as the fluid arresting effect occurring when the fluid is to pass a sharp edge, such as a micro- and/or nano-structured ridge or groove. It will however be appreciated that other suitable materials, effects or structures may be used for preventing the fluid sample from passing the portion of the working electrode and thereby provide a flow gate or stop in the channel.

According to an embodiment of the present invention, the device may comprise at least one hydrophilic surface portion. The hydrophilic surface portion, which e.g. may have a WCA below 80 degrees, such as below 50 degrees WCA, and preferably below 20 degrees WCA, may be arranged to contact the fluid sample and to cooperate with the working and/or reference electrode such that the fluid sample is enabled to pass the hydrophilic surface portion.

According to an embodiment of the present invention, the device may be adapted to apply a potential difference between the working electrode and the reference electrode. The voltage between the electrodes may be chosen such that a change of wettability may be obtained without affecting the fluid sample such that the measuring or analysis result is risked. The voltage may for example be in the range of −5 V to +5 V, and preferably in the range of −1.3 to +1.3 V.

It will be appreciated that any of the features in the embodiments described above for the device according to the first aspect of the present invention may be combined with the method according to the second aspect of the present invention.

Further objectives of, features of, and advantages with, the present invention will become apparent when studying the following detailed disclosure, the drawings and the appended claims. Those skilled in the art will realise that different features of the present invention can be combined to create embodiments other than those described in the following.

BRIEF DESCRIPTION OF THE DRAWINGS

The above, as well as additional objects, features and advantages of the present invention, will be better understood through the following illustrative and non-limiting detailed description of preferred embodiments of the present invention, with reference to the appended drawings, in which.

DETAILED DESCRIPTION

Figure 1:
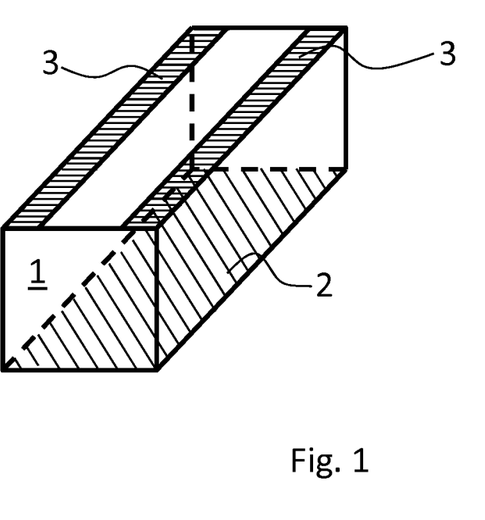
FIG. 1 is a perspective view of a channel having two longitudinal, plane reference electrodes and one ditto working electrode.

With reference to FIG. 1, there is shown a schematic view of a device for movement of a fluid sample along a flow path 1 according to an embodiment of the present invention.

The device of the present embodiment comprises a channel 1 defined by a bottom, a roof, and two sidewalls. A longitudinal, plane working electrode 2 is arranged on a surface of the bottom of the channel 1 facing the fluid. The roof is provided with two longitudinal, plane reference electrodes 3 arranged on a surface of the roof extending along, and in parallel with, the working electrode 2. Both electrodes are arranged to electrically contact the fluid sample as it moves along the channel 1.

Figure 6:
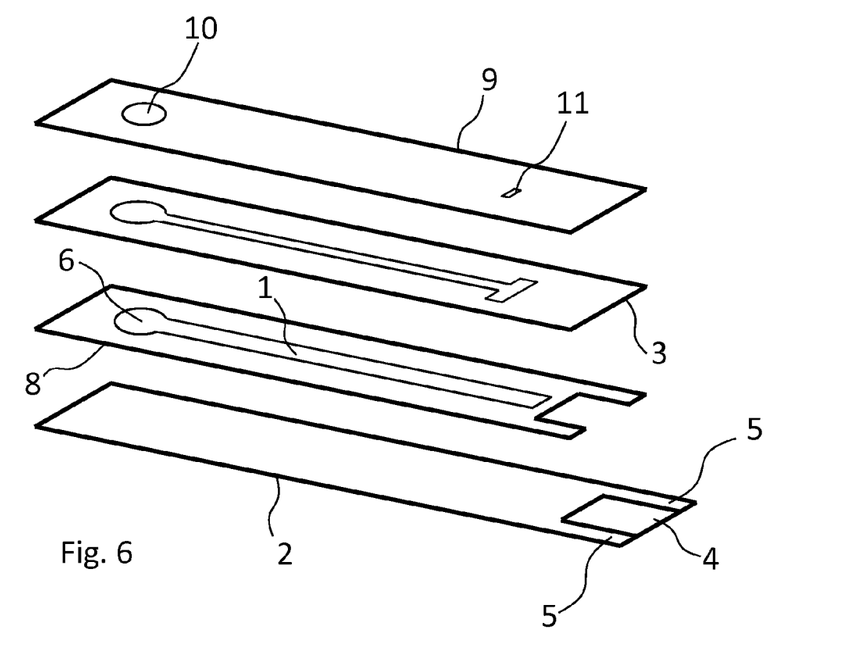
FIG. 6 is an exploded view of a device according to one example of the invention.

As shown in FIG. 6, the working electrode 2 may comprise a sputtered gold layer and be provided with contacts 5 for application of a voltage. The reference electrode 3 may be a silver electrode that is screen printed on a plastic film, also comprising a contact area 4 for electrical connection. The bottom and the roof of the channel 1 may be joined by an intermediate adhesive tape 8, defining the channel 1 in which the fluid sample may flow during use.

The device preferably comprises a sample loading hole 10 communicating with a fluid reservoir 6 arranged to receive and accommodate the fluid sample. The fluid reservoir 6 may communicate with the channel 1 such that the fluid sample may be supplied to the channel 1. A fluid outlet hole 11 is arranged such that e.g. air may be evacuated from the channel as the fluid sample is introduced in the channel 1.

The device may further comprise through connections and contact pads 4,5 for connecting the electrodes to for example an external power supply to enable the working electrode 2 to act as a wettability switch.

During use, a fluid sample volume of for example 20 μl is applied to the upstream end portion of the channel 1 via the inlet and the fluid reservoir 6. When a voltage is applied between the working electrode 2 and the reference electrode 3, for example −1.2 V, the wettability of the working electrode 2 is changed to its more hydrophilic state, inducing a movement of the fluid front.

In other words, an actuation of the fluid flow may be obtained by applying an electrical voltage between the electrodes 2, 3. The working electrode 2 may then switch to a more hydrophilic state and thereby enable the fluid to pass the electrodes. Correspondingly, a fluid flow may be stopped by from passing the working electrode 2 by removing the electrical voltage. Thereby a control of the movement, wherein the flow may be both actuated and stopped, is enabled.

Either one of, or all of the electrodes 2,3 may be provided with a structured surface comprising micro- and/or nano-structures which may increase the hydrophobic nature of the surfaces, at least in their initial, non-activated state. The microstructures and/or nanostructures may for example include the geometrical form of hills, ridges, paraboloids, pillars, or trenches.

Figure 2:
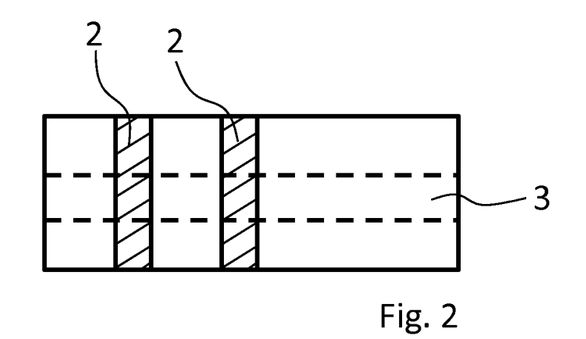
FIG. 2 is a top plan view of a channel having one longitudinal reference electrode (outline indicated by dashed lines), and two working electrodes consecutively arranged on the bottom surface of the channel.

FIG. 2 is a top plan view illustrating another embodiment of a device for movement of a fluid sample along a flow path 1, having one longitudinal plane reference electrode 3 (outline indicated by dashed lines) arranged on a surface of the roof and extending along, and in parallel with, the channel 1. According to this embodiment, a series of working electrodes 2 are arranged on the bottom of the channel 1 and connected to an external power supply in order to enable a change of wettability. The wettability of the working electrodes 2 may be individually controlled (e.g. for the use as consecutively arranged flow gates/stops in a hydrophilic capillary channel).

Figure 3:
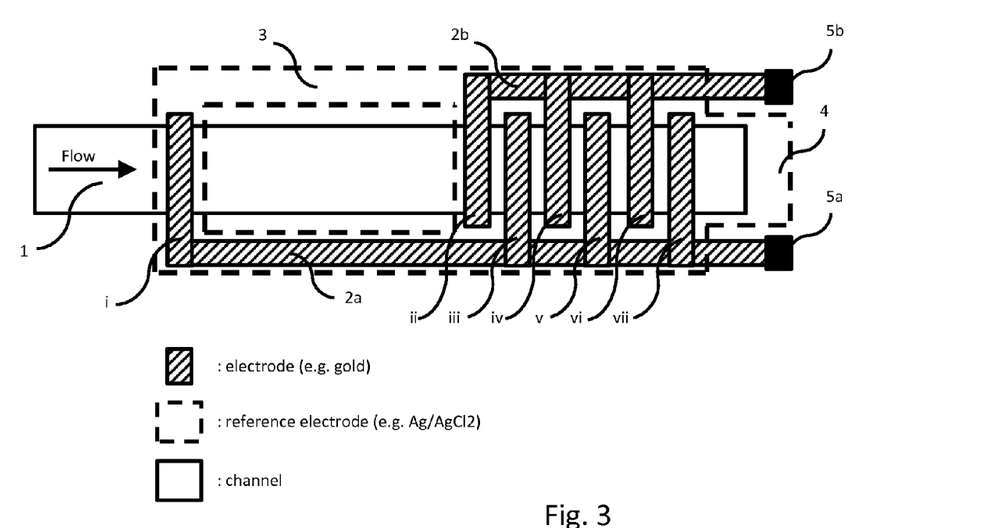
FIG. 3 shows an embodiment of the present invention wherein the channel is provided with interdigitated working electrodes arranged on the bottom of the channel and wherein a longitudinal reference electrode is arranged in the roof of the channel.

As shown in FIG. 3, an embodiment of the device may also comprise interdigitated work electrodes 2a, 2b and a longitudinal reference electrode 3, wherein at least a portion of the longitudinal reference electrode 3 is positioned abreast of or downstream at least a portion of one or several of the interdigitated work electrodes 2. According to this embodiment, two longitudinal work electrodes 2a and 2b, extending along the bottom surface of the channel 1, may share a common interdigitated area defined by transverse fingers i, ii, iii, iv, v, vi, vii consecutively arranged along the channel 1. The reference electrode 3 may be placed along the roof surface of channel 1, and may e.g. have hydrophobic surface properties. Each of the two interdigitated working electrodes 2a and 2b may have separate contact areas 5a, 5b. The wettability of the two interdigitated working electrodes 2a, 2b may be individually controlled. Each working electrode finger i, ii, iii, iv, v, vi, vii in combination with the reference electrode, which may be hydrophobic, may provide a flow gate (e.g. for the use as consecutively arranged flow gates/stops in a hydrophilic capillary channel).

When a sample fluid is added at the channel inlet, the fluid front may tend to move, e.g. by capillary flow, due to the hydrophilic nature of the channel bottom around the working electrodes, into the channel in which it may stop at the flow gate provided by the working electrode finger i. The direction of the flow is indicated by the arrow in FIG. 3. The fluid front may stay at the flow gate due to the hydrophobic properties of the working electrode in its natural state and due to the hydrophobic properties of the portion of the reference electrode placed abreast.

As a negative potential is applied to the working electrode 2a with respect to the reference electrode 3 abreast, the working electrode finger i may turn hydrophilic and enable the fluid front to pass the flow gate. The fluid front may then proceed along the channel, e.g. driven by capillary flow, and stop at the flow gate at working electrode finger ii, since it is still not activated.

When a negative potential is applied to working electrode 2b with respect to the reference electrode 3 abreast, the working electrode finger ii may turn hydrophilic and allow the fluid front to pass the flow gate. The fluid front may then move further into the channel 1, e.g. by capillary flow, and stop at the flow gate at the working electrode finger iii since said finger is still not activated.

Following the same procedure for the activation of flow gate iii-vii, the sample fluid may be moved step by step all the way through the channel.

Figure 4:
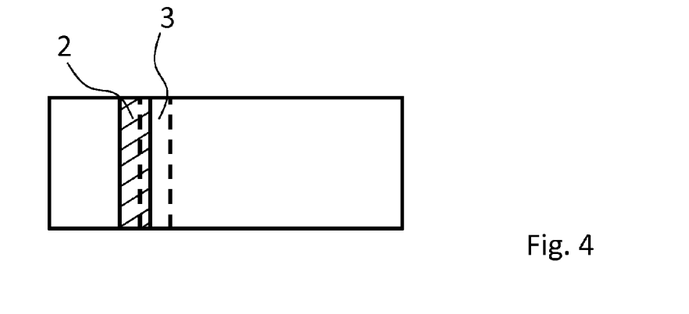
FIG. 4 is a top plan view of the channel having a reference electrode with a portion arranged abreast of a portion of the working electrode.

FIG. 4 illustrates a further embodiment of the present invention, in which a portion of a reference electrode 3 (outlined by dashed lines) is arranged abreast of a portion of a working electrode 2. The working electrode 2 may be arranged at the bottom surface, and the reference electrode 3 at roof of the channel 1.

Figure 5:
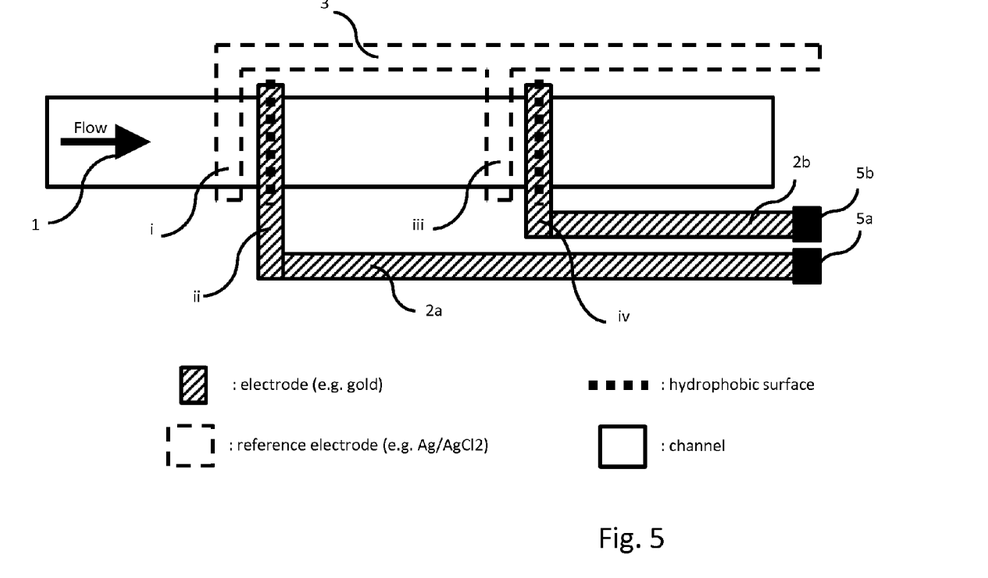
FIG. 5 shows an embodiment of the present invention wherein all electrodes are arranged on the bottom surface of the channel.

As shown in FIG. 5, an embodiment of the device may also comprise working electrodes 2a, 2b and a finger reference electrode 3 sharing a common plane or surface, wherein at least a portion of the reference electrode 3 is positioned abreast of and/or downstream at least a portion of a working electrode 2. According to this embodiment, two working electrodes 2a, 2b, and a reference electrode 3 may be extending along the bottom surface of the channel 1. The roof surface of channel 1 may be provided with hydrophobic surface portions above the working electrode fingers ii and iv.

Each one of the two working electrodes 2a, 2b may have a separate contact area 5a, 5b, respectively. The wettability of the two working electrodes 2a, 2b may be individually controlled. Each working electrode finger facing a hydrophobic surface portion in the roof may provide a flow gate (e.g. to be used as consecutively arranged flow gates/stops in a hydrophilic capillary channel).

When a sample fluid is added at the channel inlet the fluid front may start moving, e.g. by capillary flow due to the hydrophilic nature of the channel roof, proceed into the channel, pass the reference electrode finger i, and stop at the flow gate at working electrode finger ii. The direction of the movement of the fluid front is indicated by the arrow in FIG. 5. The fluid front may stay at the flow gate due to the hydrophobic properties of the working electrode in its natural state and due to the hydrophobic surface portion in the roof.

As a negative potential is applied to the working electrode 2a with respect to the reference electrode 3, the working electrode finger ii may turn hydrophilic and allow the fluid front to pass the flow gate at working electrode ii. The fluid front may then move further into the channel, e.g. by capillary flow, and pass the reference electrode finger iii, due to the hydrophilic nature of the channel roof, and stop at the flow gate at working electrode finger iv since this finger iv is still not activated.

When a negative potential is applied to working electrode 2b with respect to the reference electrode 3, the working electrode finger iv may turn hydrophilic and let the fluid front pass the flow gate at working electrode finger iv. The fluid front may then move further into the channel, e.g. by capillary flow, and stop at the end of the channel.

FIG. 6 shows an exploded view of a device according to an embodiment of the present invention. In this embodiment, a bottom layer 2 is coated with gold constituting the working electrode 2. The gold coated side of the bottom layer 2 defines the bottom of the channel 1. On top of the bottom layer 2 a self-adhesive spacer tape 8 is arranged, defining the walls of the channel 1 and the reservoir volume 6. A polymer film 9, onto which a silver reference electrode 3 is screen printed, is arranged on top of the stacked layers. The screen printed side of the polymer film 9 defines the roof of the channel 1. The electrode layers are connected to contact pads 4,5 for enabling electrical connection to an external power supply.

Figure 7:
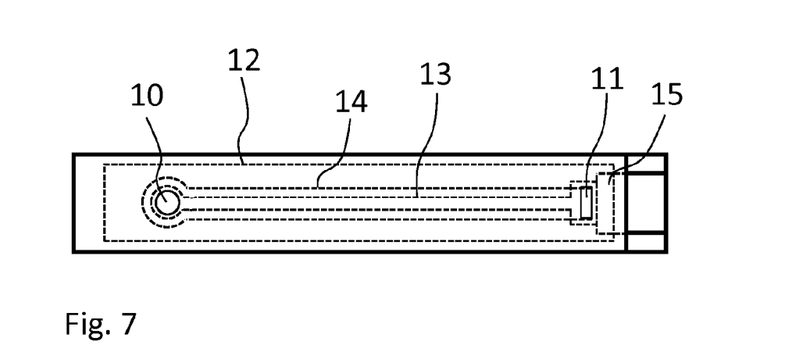
FIG. 7 is a top plan view of the device in FIG. 6, wherein the outlines of the electrodes and the channel are indicated by dashed lines.

FIG. 7 shows a top plan view of the embodiment of FIG. 6, wherein the outer boundary 12 and the inner boundary 13 of the reference electrode 3, the channel side walls 14, and an electrical through connection 15 between the reference electrode 3 and the contact area 4 for the reference electrode 3 are indicated by dashed lines.

The device according to the present invention may be used in for example biotechnological applications, such as micro-total analysis systems ('lab-on-a-chip' systems); micro-factories and chemical or biochemical micro-plants; miniaturization of chemical synthesis, biosensors; rapid DNA separation and sizing; cell manipulation and sorting; food analysis; detection of biological warfare, and diagnostic applications, such as biomarker detection; genetic analysis, typing and fingerprinting; microbial pathogen detection, and in various pharmaceutical applications.

While specific embodiments have been described, the skilled person will understand that various modifications and alterations are conceivable within the scope as defined in the appended claims.

For example, although the channels 1 described with reference to FIGS. 1-7 have a rectangular enclosing surface, it will be appreciated that, in the present invention, the channel 1 of the device is not limited to such a shape and may, for instance, have a circular cross section, or only two or three walls. Consequently, although the working electrodes 2 and the reference electrodes 3 described in the present application are plane electrodes, it will be appreciated that the electrodes 2,3 may have other shapes adapted to the shape of the inside of the channel 1 into which such electrodes 2,3 are intended to be arranged.

The embodiments are not limited to having the reference electrode 3 arranged at the roof and the working electrode 2 at the bottom of the channel 1. The electrodes might as well be arranged the other way around, i.e. the reference electrode 3 being arranged at the bottom and the working electrode 2 at the roof of the channel 1. One or several of the electrodes might also be arranged at the sidewall(s).

Example 1

The experiment described herein was done to determine the influence of reference electrode 3 placement on fluid flow length. In-house produced microfluidic chips were used for fluid flow tests to characterize electrowetting actuated fluid flow rate and length. Microfluidic chips were constructed by assembly of the following: a gold coated microscopic slide 2, a 73 µm self-adhesive spacer tape 8, a cyclo olefin polymer (COP) plastic film 9 as is, or with a screen printed silver/silver chloride reference electrode 3 facing the microchannel 1.

FIG. 6 shows the composition of the different layers of the microfluidic chips where the gold coated slide 2 make up the floor, the spacer tape 8 the walls, and the COP film 9 (including the reference electrode 3) the roof of the microfluidic channel 1. Thus, the microfluidic channel 1 or flow path 1 is here defined by a plane metallic electrode at the bottom, spacer tape 8 walls of the spacer tape 8 at the sides, and reference electrode 3 roof portions of the reference electrode 3 and a plastic film 9 roof portion of the plastic film 9. Channel geometry (width and length) was created by laser cutting the spacer tape creating a 2 mm wide channel 1 with a height of 73 µm, and length of 63 mm. A circular hole 10 allowing sample loading, and one rectangular 0.5×2 mm hole 11 for air outlet was created by laser cutting the COP film 9.

As mentioned above, in this example two chip configurations were used in order to compare the characteristics of a chip according to the invention and a chip according to the prior art. Thus, the COP film 9, i.e. the roof, was:
in chip configuration 1 used as is, i.e. without any coating, and
in chip configuration 2 coated by screen printing a silver/silver chloride reference electrode 3 onto the film 9, to serve as a reference electrode 3.

A silver/silver chloride composition for screen printing was used for screen printing the reference electrode 3. For chip configuration 1, a 0.38 mm thick silver wire was used as reference electrode 3. The chips were then assembled by allowing self-adhesive spacer tape 8 to adhere to the gold coated slides 2 followed by placement of the COP film 9 (with or without screen printed silver/silver chloride electrode 3) such that the sample loading 10 and air inlet holes aligned with the microchannel geometry of the adhesive.

Thereafter, 20 µl bovine serum was used as a fluid sample and was applied to the sample loading hole 10 of the chip using a micropipette. The fluid sample was allowed to settle in the sample loading hole 10 for 30 seconds, to allow it to wet the COP film 9 edges bordering the loading hole 10, where after minus (−) 1.2 V was applied to the working electrode 2 (i.e. the gold surface), to promote electrowetting and the subsequent flow of fluid pass the electrode surface. In chip configuration 2, the voltage was applied until the fluid had passed through the entire flow channel 1. For chip configuration 1 the voltage was applied until the fluid flow stopped.

FIG. 6 is an exploded view showing a chip assembled according to configuration 2, comprising a working or work electrode 2, i.e. gold coated slide, an adhesive layer 8, and a plastic film 9 with screen printed silver/silver chloride forming the reference electrode 3. FIG. 7 is a top view showing a sample loading hole 10, an outer and inner boundary of the silver or reference electrode 3, a channel 1 side wall, and a contact areas 4, 5 for the reference and working electrodes 3, 2.

When using chips according to configuration 2, minus (−) 1.2 V for 25 seconds was sufficient to allow the sample to enter and flow across the entire channel 1. In contrast, chips according to configuration 1 (i.e. with the reference electrode 3 placed upstream of the flow channel 1) did not allow the fluid to reach halfway through the channel 1, not even after applying voltage for an additional minute. When looking at the flow rate across the entire flow length for chips according to configuration 1 (average flow length was 25 mm), it could be noted that the fluid rate was diminishing rapidly. An initial flow rate of 1.3-1.4 mm/s quickly dropped to 0.2-0.3 mm/s. Thus, it appears that electrowetting actuated flow only may occur for the first 10 mm while the remainder of the flow may occur by passive flow that may not be affected by the applied voltage. The fluid may eventually stop before halfway through the channel 1, maybe due to lowering of the voltage potential across the fluid front as the resistance of fluid contained within the channel 1 increases with fluid flow length. After electrowetting actuated flow ceased (approximately 10 mm) the fluid continues to travel to the point where the so called viscous resistance counteracts the capillary force. For chips according to configuration 2, having a reference electrode 3 placed parallel to, and at essentially constant distance from, the working electrode 2 did not experience any fluid flow length limitations, i.e. the flow seems not to be affected by the flow path length, and flow rate dropped only marginally across the 63 mm long channel 1, and seldom below 1.8 mm/s. Thus, for chips according to the embodiment of the invention, having the reference electrode 3 and working electrode 2 arranged along the flow path 1 to contact the fluid sample along the path, a controlled and reliable flow of the fluid sample may be obtained.

Importantly, contact angle measurements showed that the screen printed silver electrode surface was more hydrophobic than the COP film. The contact angle for the silver electrode was around 120° measured 30 seconds after applying 20 µl bovine serum, while the COP film exhibited a contact angle of around 90° for the same sample. Thus, chip configuration 2 presents a greater resistance to capillary flow compared to configuration 1 (without a screen printed reference electrode 3).

Altogether, the arrangement of the reference and working electrode 2 of the device according to the embodiment described herein may prevent loss/lowering of the voltage potential across the fluid front, why fluid flow length limitations may be, if not completely abolished, at least substantially advanced, and not markedly limited by the viscous resistance.

Example 2

The experiment described herein was done to further examine and characterise the influence of reference electrode 3 placement on electrowetting actuated fluid flow rate and flow length.

Microfluidic chips were constructed by assembly of the following:
i) Cyclo-olefin polymer (COP) plastic film 9:
  a. 188 µm thick
    i. sputter coated with titanium and gold (50 Å titanium and 1000 Å gold)
  b. 100 µm thick
    i. as is
    ii. with a screen printed silver/silver chloride reference electrode 3 facing the microchannel 1
ii) 73 µm self-adhesive spacer tape 8.

Chip layers were assembled as described in Example 1. 20 µl bovine serum was used as fluid sample and was applied to the sample loading hole 10 of each chip using a micropipette. The fluid sample was allowed to settle in the sample loading hole for 30 seconds, to allow it to wet the COP film 9 edges bordering the loading hole 10, where after minus (−) 1.2 V was applied to the working electrode 2 (i.e. the gold surface), to promote electrowetting and the subsequent flow of fluid pass the electrode surface. Voltage was thereafter applied according to a pre-programmed scheme.

Figure 8:
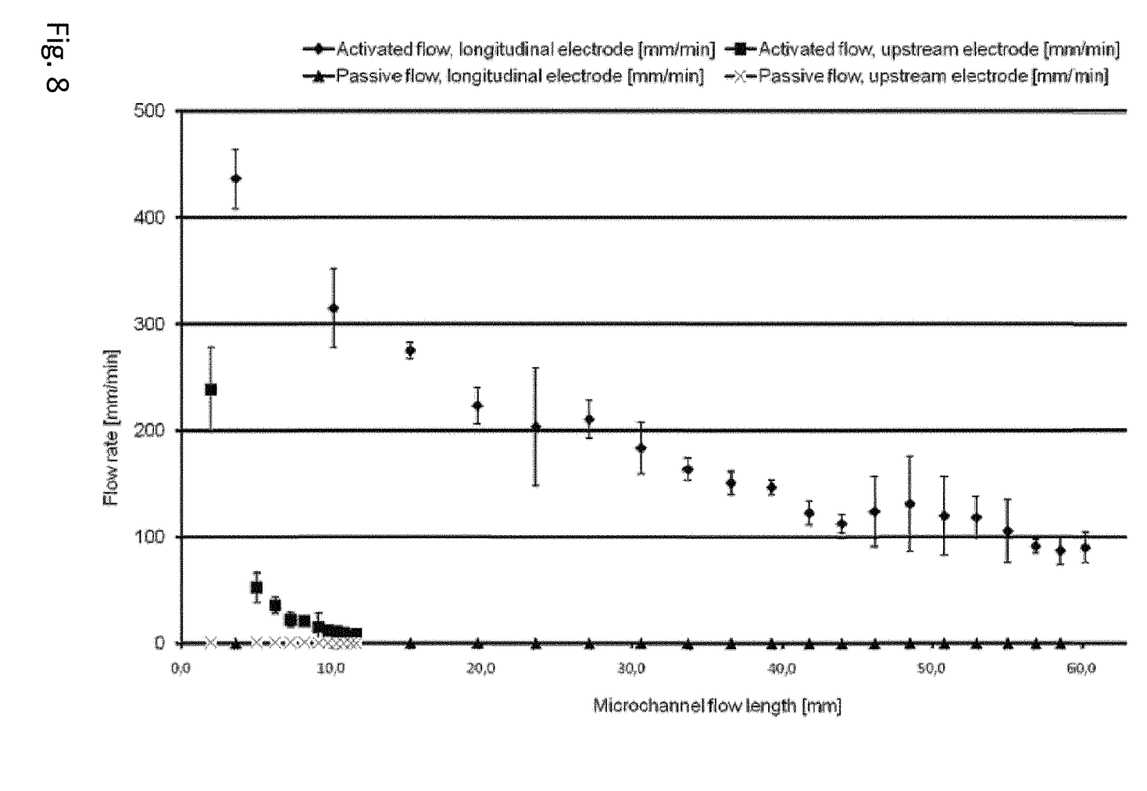
FIG. 8 is a diagram showing discrete flow rates for an embodiment of the invention as compared to prior art.

Chips according to configuration 1 (with upstream, silver wire electrode) and configuration 2 (with longitudinal electrodes or electrodes arranged along the flow path 1) as described in Example 1 were used for the experiment. Short 1 second pulses with minus (−) 1.2 V (followed by a 30 second waiting period) were applied repeatedly, to allow discrete flow rates along the entire distance travelled by the fluid to be measured. Reference is made to FIG. 8 showing a diagram of the flow rate against microchannel flow length. Results are shown for activated flow for a longitudinal reference electrode, activated flow for an upstream reference electrode, passive flow for a longitudinal reference electrode and passive flow for an upstream reference electrode.

Chips with an upstream, silver wire electrode supported electrowetting actuated fluid flow for no more than 10 mm, and an initial fluid of 240 mm/min rapidly dropped tenfold to 24 mm/min after a distance of only 7 mm. After 10 mm fluid flow was down to 10 mm/min, which was barely noticeable by visual inspection. This is in agreement with the results from the experiment described in Example 1, where it appeared that electrowetting actuated flow only occurred for the first 10 mm while the remainder of the flow seemed to occur by passive flow.

Chips having a reference electrode 3 placed parallel to, and at constant distance from, the working electrode 2 (i.e. according to configuration 2) did not experience any fluid flow length limitations, and flow rate dropped only 5 fold at most and plateaued at 100 mm/min at the end of the 63 mm long channel 1, which is in agreement with the results obtained in the experiment described in Example 1 (where minimal flow was 1.8 mm/s, which is equal to 108 mm/min). Thus, altogether we argue that placing the reference electrode 3 of microfluidic systems according to the current invention substantially improves microfluidic flow rates and pushes the boundaries for fluid flow length to a point where the development of a variety of microfluidic applications is enabled and such microfluidic chips became realizable.

The invention claimed is:

1. A device for controlling movement of a fluid sample along a flow path comprising:
   a channel defining the flow path, said channel comprising a first surface, an opposite surface including a channel roof, and two sidewalls,
   a working electrode arranged on said first surface to contact the fluid sample when said fluid sample moves along the flow path;
   a reference electrode arranged to directly contact the fluid sample when said fluid sample moves along the flow path; and
   a hydrophobic surface portion arranged to directly contact the fluid sample when said fluid sample moves along the flow path;
   wherein at least a portion of said reference electrode is arranged abreast of or downstream at least a portion of said working electrode, and wherein said hydrophobic surface portion is arranged on said opposite surface and abreast of at least a portion of the working electrode and said hydrophobic surface portion covers a portion of the channel roof of the channel and arranged after the reference electrode in the direction of the flow path, and wherein at least another portion of the channel roof is of hydrophilic nature.

2. The device according to claim 1, wherein the working electrode and/or the reference electrode is/are plane electrode(s).

3. The device according to claim 1, wherein the working electrode and the reference electrode extend in separate planes.

4. The device according to claim 3, wherein the working electrode and the reference electrode are arranged opposite to each other.

5. The device according to claim 1, wherein the working electrode and/or the reference electrode comprise(s) a structured surface adapted to contact the fluid sample.

6. The device according to claim 5, further comprising at least one hydrophilic surface portion arranged to contact the fluid sample and wherein at least a portion of said hydrophilic surface portion is arranged abreast of at least a portion of the working and/or reference electrode.

7. The device according to claim 1 wherein the working electrode and/or the reference electrode is/are longitudinal electrode(s) in relation to the flow path.

8. The device according to claim 1, comprising at least two working electrodes and/or at least two reference electrodes which are consecutively arranged along the flow path.

9. The device according to claim 1, comprising at least two working electrodes and/or at least two reference electrodes which are interdigitated electrodes.

10. The device according to claim 1, wherein the device further comprises a fluid reservoir arranged to receive and accommodate the fluid sample, wherein the fluid sample has a fluid front, and from where the fluid front moves along the flow path.

11. The device according to claim 1, wherein the working electrode and/or the reference electrode(s) comprise(s) at least a surface comprising a material selected from the group consisting of gold, platinum, iridium, osmium, silver, palladium, graphite, graphene, and fullerenes.

12. The device according to claim 1, further adapted to apply a voltage between the reference electrode and the working electrode, wherein the voltage is within the range of −5V to 5 V.

13. The device according to claim 12, wherein the voltage is within the range of −1.3 V to 1.3 V.

14. The device according to claim 1, wherein the working electrode and/or the reference electrode comprise(s) a structured micro- and/or nano-structured surface adapted to contact the fluid sample.

15. A method for controlling movement of a fluid sample along a flow path, wherein the method comprises the steps of:
  providing a channel defining the flow path;
  providing a working electrode arranged to contact the fluid sample when said fluid sample moves along the flow path;
  providing a reference electrode arranged to contact the fluid sample when said fluid sample moves along the flow path;
  providing a hydrophobic surface portion arranged to contact the fluid sample when said fluid sample moves along the flow path;
  wherein at least a portion of said reference electrode is arranged abreast of or downstream at least a portion of said working electrode, and wherein at least a portion of said hydrophobic surface portion is arranged abreast of and opposite at least a portion of said working electrode and said hydrophobic surface portion covers a portion of a channel roof of the channel and arranged after the reference electrode in the direction of the flow path and at least another portion of the channel roof is of hydrophilic nature.

* * * * *